United States Patent [19]

Onizuka et al.

[11] Patent Number: 4,683,211
[45] Date of Patent: * Jul. 28, 1987

[54] METHOD FOR MEASURING THE CONCENTRATION OF $CaCO_3$ IN A SLURRY

[75] Inventors: Masakazu Onizuka; Atsushi Tatani; Takayoshi Hamada, all of Hiroshima, Japan

[73] Assignee: Mitsubishi Jukogyo Kabushiki Kaisha, Tokyo, Japan

[*] Notice: The portion of the term of this patent subsequent to Jun. 30, 2004 has been disclaimed.

[21] Appl. No.: 638,512

[22] Filed: Aug. 7, 1984

[30] Foreign Application Priority Data

Aug. 10, 1983 [JP] Japan ................... 58-144895

[51] Int. Cl.$^4$ ............... G01N 1/00; G01N 33/00; G01N 35/00
[52] U.S. Cl. ................................. 436/50; 436/52; 436/55; 436/79; 436/133; 436/146; 436/175; 436/179; 436/181
[58] Field of Search .............. 436/43, 50, 51, 52, 436/55, 79, 127, 133, 146, 163, 174, 175, 177, 179, 181

[56] References Cited

U.S. PATENT DOCUMENTS

| | | | |
|---|---|---|---|
| 3,459,938 | 8/1969 | Stenger et al. | 436/146 |
| 3,801,281 | 4/1974 | Thompson et al. | 436/133 X |
| 4,046,510 | 9/1977 | Becker et al. | 436/146 |
| 4,061,467 | 12/1977 | Becker et al. | 436/179 X |
| 4,063,891 | 12/1977 | Becker et al. | 436/146 |
| 4,236,960 | 12/1980 | Hultman et al. | 436/55 X |
| 4,397,957 | 8/1983 | Allison | 436/133 |

FOREIGN PATENT DOCUMENTS 96450   7/1980   Japan ................... 436/146

Primary Examiner—David E. Lacey
Assistant Examiner—Robert J. Hill, Jr.
Attorney, Agent, or Firm—Birch, Stewart, Kolasch & Birch

[57] ABSTRACT

A method for continuously measuring the concentration of $CaCO_3$ in slurries comprising $CaCO_3$ is described. The method comprises continuously sampling a given amount of the slurry, feeding the sampled slurry into an agitated continuous reactor container which is isolated from the outside air, keeping the slurry in the reactor container at a temperature of at least 50° C., adding sulfuric acid or hydrochloric acid to adjust the pH to below 4, blowing a known flow rate of air into the slurry, withdrawing from the reactor container $CO_2$, produced by the reaction between $CaCO_3$ and the acid, by entrainment with the air, further mixing the withdrawn gas with air for dilution while controlling a flow rate of the dilution air so that the concentration of $CO_2$ in the mixed gas is maintained constant, and calculating the concentration of $CaCO_3$ in the slurry from the concentration of $CO_2$ in the mixed gas, the flow rate of the mixed gas and the amount of the sampled slurry.

8 Claims, 2 Drawing Figures

METHOD FOR MEASURING THE CONCENTRATION OF CACO₃ IN A SLURRY

BACKGROUND OF THE INVENTION

1. Field of the Invention

This invention relates to a method for continuously measuring a concentration of $CaCO_3$ in slurries comprising $CaCO_3$ such as, for example, an absorption liquid slurry used in flue gas desulfurization systems using a wet lime process.

2. Description of the Prior Art

The concentration of $CaCO_3$ in an absorption solution used in flue gas desulfurization systems using a wet lime process has been heretofore measured by manual analysis. This manual analysis is disadvantageous in requiring hands and time.

SUMMARY OF THE INVENTION

An object of the invention is to eliminate the above disadvantages and to provide a method for accurately measuring a concentration of $CaCO_3$ in slurries within a short time and in an continuous manner.

The present invention provides a method for continuously measuring the concentration of $CaCO_3$ in slurries comprising $CaCO_3$, the method comprising:

continuously sampling a given amount of the slurry;
feeding the sampled slurry into an agitated continuous reactor container which is isolated from the outside air;
keeping the slurry in the reactor container at a temperature of at least 50° C.;
adding sulfuric acid or hydrochloric acid to adjust the pH to below 4;
blowing a known flow rate of air into the slurry;
withdrawing from the reactor container $CO_2$, produced by the reaction between $CaCO_3$ and the acid, by entrainment with the air;
further mixing the withdrawn gas with air for dilution while controlling a flow rate of the dilution air so that the concentration of $CO_2$ in the mixed gas is maintained constant; and
calculating the concentration of $CaCO_3$ in the slurry from the concentration of $CO_2$ in the mixed gas, the flow rate of the blown air, the flow rate of the dilution air and the amount of the sampled slurry.

DETAILED DESCRIPTION AND EMBODIMENTS OF THE INVENTION

Figure 1:
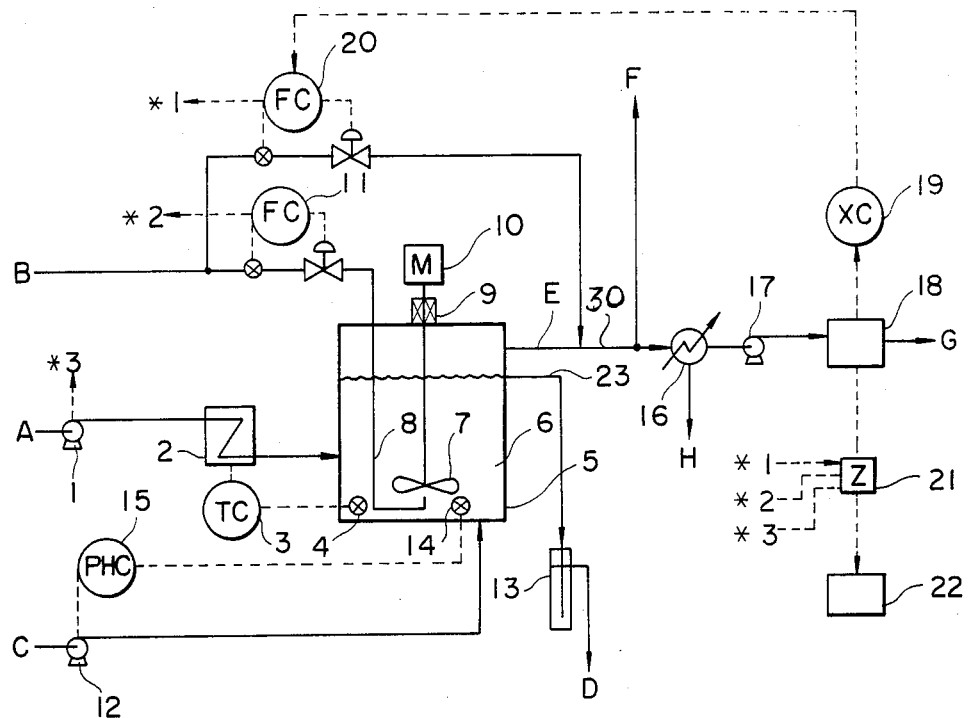
FIG. 1 is a flowchart of a method according to the invention.

Reference is now made to FIG. 1 which illustrates one embodiment of the invention.

In FIG. 1, there is shown a flowchart of a test plant of measuring a concentration of $CaCO_3$ in which indicated at A is a sample slurry, at B is air, at C is sulfuric acid (or hydrochloric acid), at D is a waste liquor, at E is a withdrawn gas consisting of air containing $CO_2$, at F is an exhaust, at G is an exhaust, and at H is drain. Moreover, indicated at 1 is a fixed displacement pump, at 2 is a heater, at 3 is a temperature controller, at 4 is a temperature detector, a 5 is an agitated continuous reactor container which is a closed system or is isolated from the outside air, at 6 is a resident liquid, at 7 is an agitator, at 8 is an air blowing pipe, at 9 is a sealing material, at 10 is a motor, at 11 is a flow controller, at 12 is a delicate pump, at 13 is a liquid sealing device, at 14 is a pH electrode, at 15 is a pH adjuster, at 16 is a dehumidifier, at 17 is an air pump, at 18 a $CO_2$ analyzer, at 19 is a $CO_2$ concentration setting device, at 20 is a secondary air flow rate controller, at 21 is an operator, at 22 is an indicator, at 23 is an overflow pipe, and at *1, *2 and *3 are signals.

In operation, a given amount of sample slurry A comprising $CaCO_3$ is sampled by the fixed displacement pump 1 and is heated through the heater 2 which is controlled by the signal from the temperature controller 3 after detection of a temperature of the resident liquid 6 in the reactor container 5 with the detector 4 so that the temperature of the resident liquid 6 is kept at a predetermined temperature (50° C.), followed by feeding to the reactor container 5. The pH of the liquid 6 in the reactor container 5 is checked by the use of the pH detector 14 and the delicate pump 12 is controlled by the signal from the pH adjuster 15. As a consequence, sulfuric acid (or hydrochloric acid) is introduced into the reactor container 5 and the pH in the system is adjusted to a predetermined level (below 4). It will be noted that the upper limit of the temperature of the resident liquid 6 is a boiling point of the resident liquid and the pH is preferably controlled to be in the range of from 2 to 4.

During the operation, $CO_2$ is generated according to the following reaction (1) or (2).

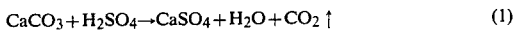

$$CaCO_3 + H_2SO_4 \rightarrow CaSO_4 + H_2O + CO_2 \uparrow \quad (1)$$

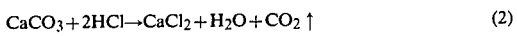

$$CaCO_3 + 2HCl \rightarrow CaCl_2 + H_2O + CO_2 \uparrow \quad (2)$$

In order to smoothly remove the generated $CO_2$, air B whose flow rate is controlled at a given level by means of the flow controller 11 is blown through the air blowing pipe 8 into the resident liquid 6. At the same time, the resident liquid 6 is agitated by means of the agitator 7 driven through the sealing material 9 by the motor 10 so that the solid matters contained in the resident liquid 6 in the reactor container 5 do not settle.

An excess of the resident liquid 6 resulting from the feed of sample slurry from the fixed displacement pump 1 is discharged from the overflow pipe 23 into the liquid sealing device 13, in which the liquid level is so controlled as to overcome the inner pressure of the reactor container 5, thus preventing leakage of the $CO_2$-containing gas E (withdrawn gas) in the reactor container 5 by entrainment with the overflow. In addition, the sealing device 13 is so designed that the solid matters in the overflow do not settle. The excess of the overflow charged into the liquid sealing device 13 is discharged as waste liquor D.

The withdrawn gas E consisting of the $CO_2$ generated according to the reaction equation (1) or (2), and the air and evaporated moisture from the air blowing pipe 8 is combined with secondary air at 30 (air for dilution) whose flow rate is controlled with the secondary air flow controller at a preset value controlled by a $CO_2$ concentration signal described hereinafter. Thereafter, the combined mixture is released as exhaust F. In this connection, part of the exhaust F is subjected to the dehumidifier 16 to remove the moisture therefrom as drain H and then sucked by the air pump 17 in the $CO_2$ analyzer 18 in which the concentration of $CO_2$ in the exhaust is measured, followed by discharging as exhaust G.

One of detection signals from the $CO_2$ analyzer 18 is fed to the $CO_2$ concentration setter 19 by which the preset flow rate is the secondary air flow controller 20 is so controlled that the detected concentration of $CO_2$ reaches preset concentration of $CO_2$. Another signal from the $CO_2$ concentration setter 18 is fed to the operator 21 for calculation of a concentration of $CaCO_3$ in the sampled slurry A. To the operator 21 are also inputted flow signal *2 from the air flow meter 11, flow signal *1 from the secondary air flow controller 20 and flow signal *3 from the fixed displacement pump 1 for the sampling of slurry. These four input signals are logically operated in the operator 21 according to the following equation, thereby determining a concentration of $CaCO_3$ in the sampled slurry A. The concentration of $CaCO_3$ is indicated by the $CaCO_3$ concentration indicator 22.

$$\text{Concentration of } CaCO_3 \text{ [mol/l]} = \left( \frac{x}{100 - x} \right) \left( \frac{(Q_1 + Q_2)}{22.4 \times F} \right) \quad (3)$$

$Q_1$: flow rate of blown air [Nl/min]
$Q_2$: flow rate of secondary air [Nl/min]
F: flow rate of slurry being sampled [l/min]
x: concentration of $CO_2$ [vol%]

As described before, according to the invention, it is possible to continuously detect a concentration of $CaCO_3$ in slurry even though the concentration of $CaCO_3$ in slurry widely varies.

Figure 2:
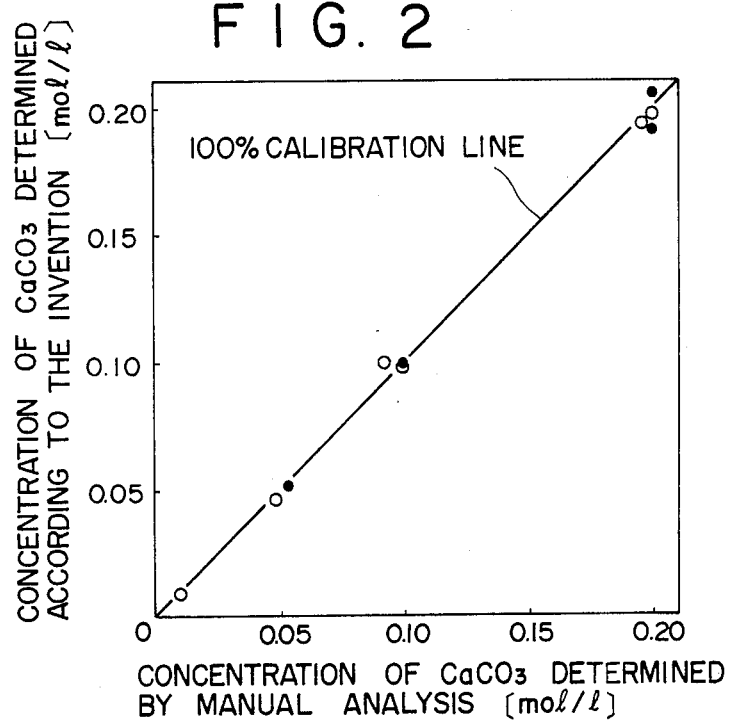
FIG. 2 is a graphical representation of the relationship between measured value of $CaCO_3$ concentration (mol/vol) determined according to the method of the invention and value determined by known manual analysis.

The present invention is more particularly described by way of example with reference to FIGS. 1 and 2. A test plant shown in FIG. 1 was used to effect a test under the following conditions.

Concentration of $CaCO_3$ in sample slurry: 0.01, 0.05, 0.1, 0.2 mol/l
Amount of sample slurry: 0.12 l/min
Total flow rate of air: 7 Nl/min
Setting of reaction temperature: 50° C.
Setting of pH for reaction: 4
Preset concentration of $CO_2$: 2 vol%
Reactor container: 1 liter in capacity The results of the measurement shown in FIG. 2 were obtained. In FIG. 2, the values detected by the method of the invention are indicated as circles in relation to the analytical values obtained by known manual analysis, in which the mark "solid circle" indicates the results using hydrochloric acid and the mark "simple circle" indicates the results using sulfuric acid. The test was effected using four different concentrations of $CaCO_3$ in slurry, and typical results of the measured value of $CO_2$, flow rate of secondary air, manually analytical value of $CaCO_3$, and detected value of $CaCO_3$ are shown in the following table.

| Items and Unit | Test No. | | | |
|---|---|---|---|---|
| | 1 | 2 | 3 | 4 |
| Concentration of $CaCO_3$ mol/l by manual analysis | 0.0094 | 0.053 | 0.101 | 0.196 |
| Concentration of $CaCO_3$ mol/l according to invention | 0.009 | 0.052 | 0.098 | 0.193 |
| Measured value of $CO_2$ vol % concentration | 0.35 | 1.95 | 2.02 | 2.02 |
| Flow rate of secondary air Nl/min | 0.0 | 0.0 | 5.8 | 18.2 |

As will be appreciated from the foregoing, according to the invention, it becomes possible to accurately measure a concentration of $CaCO_3$ in slurry within a short time and in a continuous manner.

It should be noted that the present invention is not limited to the example described above and various variations and modifications may be possible without departing from the scope and spirit of the present invention.

What is claimed is:

1. A continuous method for measuring the concentration of $CaCO_3$ in a slurry containing $CaCO_3$, the steps consisting essentially of:

continuously sampling a given amount of the slurry;
feeding the sampled slurry at a predetermined flow rate into an agitated continuous reactor container which is isolated from outside air;
maintaining the sampled slurry in the reactor container at a temperature of at least 50° C.;
adding an acid to the reactor container to adjust the pH of the slurry therein to below 4, said acid reacting with $CaCO_3$ to form a reaction product and to generate $CO_2$;
blowing a predetermined flow rate of air into the slurry in the reactor container;
withdrawing gas from the reactor container wherein the withdrawn gas comprises the blown air with generated $CO_2$ entrained therein;
diluting the withdrawn gas with air while controlling the flow rate of the dilution air so that the $CO_2$ concentration in said diluted withdrawn gas is maintained constant;
determining the flow rate of the diluted withdrawn gas;
passing the diluted withdrawn gas with generated $CO_2$ entrained therein into a $CO_2$ analyzer;
measuring the concentration of entrained $CO_2$ in the diluted withdrawn gas; and
determining the concentration of $CaCO_3$ in the slurry from the concentration of entrained $CO_2$ in the diluted withdrawn gas, the flow rate of the diluted withdrawn gas and the flow rate of the sampled slurry, wherein said continuous method is a high speed continuous method capable of measuring the concentration of $CaCO_3$ in an absorption solution used for pH control of a desulfurization system.

2. The method according to claim 1, wherein the slurry in the reactor container is maintained at a temperature in the range of from 50° C. to the boiling point of the slurry in the reactor container.

3. The method according to claim 1, wherein the pH of the slurry in the reactor container is adjusted to a value of from 2 to 4.

4. The method according to claim 1, wherein the acid is selected from the group consisting of sulfuric acid and hydrochloric acid.

5. A continuous method for measuring the concentration of $CaCO_3$ in a slurry containing $CaCO_3$, the steps consisting essentially of:

continuously sampling a given amount of the slurry;

feeding the sampled slurry at a predetermined flow rate into an agitated continuous reactor container which is isolated from outside air;

maintaining the sampled slurry in the reactor container at a temperature of at least 50° C.;

adding an acid to the reactor container to adjust the pH of the slurry therein to below 4, said acid reacting with $CaCO_3$ to form a reaction product and to generate $CO_2$;

blowing a predetermined flow rate of air into the slurry in the reactor container;

withdrawing gas from the reactor container wherein the withdrawn gas comprises the blown air with generated $CO_2$ entrained therein;

diluting the withdrawn gas with additional air while controlling a flow rate of the dilution air so that the $CO_2$ concentration in said diluted withdrawn gas is maintained constant;

passing the diluted withdrawn gas with generated $CO_2$ entrained therein into a $CO_2$ analyzer;

measuring the concentration of entrained $CO_2$ in the diluted withdrawn gas; and determining the concentration of $CaCO_3$ in the slurry from the concentration of entrained $CO_2$ in the diluted withdrawn gas, the flow rate of the blown air, the flow rate of the dilution air and the flow rate of the sampled slurry, wherein said continuous method is a high speed continuous method capable of measuring the concentration of in an absorption solution used for pH control of a desulfurization system.

6. The method according to claim 5, wherein the slurry in the reactor container is maintained at a temperature in the range of from 50° C. to the boiling point of the slurry in the reactor container.

7. The method according to claim 5, wherein the pH of the slurry in the reactor container is adjusted to a value of from 2 to 4.

8. The method according to claim 5, wherein the acid is selected from the group consisting of sulfuric acid and hydrochloric acid.

* * * * *